US011913882B2

(12) United States Patent
Cardarelli et al.

(10) Patent No.: US 11,913,882 B2
(45) Date of Patent: Feb. 27, 2024

(54) DETERMINATION OF THE SUPRAMOLECULAR ORGANIZATION OF ENCAPSULATED MOLECULES BY LUMINESCENCE LIFETIME ANALYSIS

(71) Applicants: SCUOLA NORMALE SUPERIORE, Pisa (IT); UNIVERSITÀ DEGLI STUDI DI ROMA "LA SAPIENZA", Rome (IT); FONDAZIONE ISTITUTO ITALIANO DI TECNOLOGIA, Genoa (IT)

(72) Inventors: Francesco Cardarelli, Pisa (IT); Fabio Beltram, Pisa (IT); Paolo Maria Tentori, Genoa (IT); Giulio Caracciolo, Rome (IT); Daniela Pozzi, Rome (IT)

(73) Assignees: SCUOLA NORMALE SUPERIORE, Pisa (IT); UNIVERSITÀ DEGLI STUDI DI ROMA "LA SAPIENZA", Rome (IT); FONDAZIONE ISTITUTO ITALIANO DI TECNOLOGIA, Genoa (IT)

( * ) Notice: Subject to any disclaimer, the term of this patent is extended or adjusted under 35 U.S.C. 154(b) by 0 days.

(21) Appl. No.: 18/252,202

(22) PCT Filed: Nov. 8, 2021

(86) PCT No.: PCT/IB2021/060300
§ 371 (c)(1),
(2) Date: May 9, 2023

(87) PCT Pub. No.: WO2022/097108
PCT Pub. Date: May 12, 2022

(65) Prior Publication Data
US 2023/0341326 A1 Oct. 26, 2023

(30) Foreign Application Priority Data

Nov. 9, 2020 (IT) .................. 102020000026699

(51) Int. Cl.
*G01N 21/64* (2006.01)
*G01N 33/15* (2006.01)

(52) U.S. Cl.
CPC ......... *G01N 21/6408* (2013.01); *G01N 33/15* (2013.01)

(58) Field of Classification Search
None
See application file for complete search history.

(56) References Cited

U.S. PATENT DOCUMENTS

| 10,191,060 | B2* | 1/2019 | Chiu | .................. G01N 33/587 |
| 2012/0276578 | A1 | 11/2012 | Stringari et al. | |
| 2021/0315826 | A1* | 10/2021 | Abbaspourrad | ....... G01N 33/52 |

FOREIGN PATENT DOCUMENTS

WO 2013106733 A1 7/2013

OTHER PUBLICATIONS

Yechezkel Barenholz, Liposome Application: Problems and Prospects, Current Opinion in Colloid & Interface Science, 2001, pp. 66-77 vol. 6 No.1.

(Continued)

*Primary Examiner* — David P Porta
*Assistant Examiner* — Djura Malevic
(74) *Attorney, Agent, or Firm* — Bayramoglu Law Offices LLC

(57) ABSTRACT

A determination of supramolecular organization in a substance includes target molecules and nanocarriers at least one of which is luminescent, based on a step of collecting of lifetime decay data of at least a standard substance pure or substantially pure where a known organization state of the (Continued)

target molecules and the nanocarriers is pure or substantially pure; and a step of comparing the standard data and test data from a test substance.

8 Claims, 3 Drawing Sheets

(56) References Cited

OTHER PUBLICATIONS

Upendra Bulbake, et al., Liposomal Formulations in Clinical Use: An Updated Review, Pharmaceutics, 2017, pp. 1-33, vol. 9 No. 12.

Wenlei Jiang, et al., In vitro and in vivo characterizations of PEGylated liposomal doxorubicin, Bioanalysis, 2011, pp. 333-344, vol. 3 No. 3.

Sunil Shah, et al., Photophysical characterization of anticancer drug Valrubicin in rHDL nanoparticles and its use as an imaging agent, J Photochem Photobiol B., 2016, pp. 1-19, vol. 155.

Michelle A. Digman, et al., The Phasor Approach to Fluorescence Lifetime Imaging Analysis, Biophysical Journal: Biophysical Letters, 2008, pp. 14-16.

Xiaohui Wei, et al., Cardinal Role of Intraliposome Doxorubicin-Sulfate Nanorod Crystal in Doxil Properties and Performance, ACS Omega, 2018, pp. 2508-2517, vol. 3.

Jianpeng Hao, et al., Encapsulation of the flavonoid quercetin with chitosan-coated nanoliposomes, LWT—Food Science and Technology, 2017, pp. 37-44, vol. 85.

Omar Lozano, et al., Nanoencapsulated Quercetin Improves Cardioprotection during Hypoxia-Reoxygenation Injury through Preservation of Mitochondrial Function, Oxidative Medicine and Cellular Longevity, 2019, pp. 1-14.

Xiang Gao, et al., Anticancer effect and mechanism of polymer micelle-encapsulated quercetin on ovarian cancer, Nanoscale, 2012, pp. 7021-7030 vol. 4.

Jiangtao Zhou, et al., The role of xanthophylls in the supramolecular organization of the photosynthetic complex LHCII in lipid membranes studied by high-resolution imaging and nanospectroscopy, BBA—Bioenergetics, 2019, pp. 1-20.

* cited by examiner

DETERMINATION OF THE SUPRAMOLECULAR ORGANIZATION OF ENCAPSULATED MOLECULES BY LUMINESCENCE LIFETIME ANALYSIS

CROSS REFERENCE TO THE RELATED APPLICATIONS

This application is the national phase entry of International Application No. PCT/IB2021/060300, filed on Nov. 8, 2021, which is based upon and claims priority to Italian Patent Application No. 102020000026699, filed on Nov. 9, 2020, the entire contents of which are incorporated herein by reference.

TECHNICAL FIELD

The present invention refers to methods for assessing one or more organization states of molecules and nanocarriers within a substance based on lifetime decay analysis data.

BACKGROUND

Nanoparticles, nanocapsules, nanocarriers and other similar structures have an enormous range of potential and actual applications. These structures are used to encapsulate different molecules resulting in preparations having a specific supramolecular organization that are used in several technical fields ranging from medicine, diagnostic, nutraceutical, cosmetic, textile, production of special paints dyes and inks.

In medicine, the use of nanocarriers, such as liposomes, as drug delivery carriers for medicaments and in particular for chemotherapeutic agents offers a means of modulating drug distribution to increase drug efficacy and reduce cytotoxicity. As an example, drug liposomal formulations (Gregoriadis—U, Y. B. Liposomes Problems and Prospects. 66-77 (2001)), potentially guarantee selected advantages, such as: (i) prolonged drug circulation time (with avoidance of the Reticuloendothelial system, RES), (ii) a protective lipid bilayer to increase drug stability (iii) stable loading of a high concentration of drug molecules. Drugs with different solubility can be encapsulated in liposomes, hydrophobic drugs have affinity to the phospholipid bilayer and hydrophilic drugs are entrapped in the aqueous cavity. In spite of these potential advantages, relatively few liposomal drug formulations successfully entered the clinical practice (Bulbake, U., Doppalapudi, S., Kommineni, N. & Khan, W. Liposomal formulations in clinical use: An updated review. Pharmaceutics 9, 1-33 (2017)) The first and successful milestone in liposome-based products was the introduction of the PEGylated liposomal doxorubicin product Doxil®. This is the first FDA-approved nano-drug (1995) and is currently used for the treatment of a number of pathologies, including AIDS-related Kaposi's sarcoma in patients with HIV, recurrent ovarian cancer, metastatic breast cancer, multiple myeloma. Doxil® consists of a formulation of 85-nm-diameter liposomes with 2000-Da segments of poly-(ethylene glycol) (PEG) engrafted onto the liposome surface and loaded with doxorubicin (hereafter DOX). Doxil® performance proved to be superior with respect to isolated DOX, but, almost 10 years after Doxil-related patents expired, there is still no FDA- or EMA-approved generic "Doxil" available. As clearly pointed out by both Y. Barenholz (Doxil's inventor) and W. Jiang (Office of Generic Drugs of the FDA), a major cause, at the very bottom, is the limited understanding of the "synthetic identity" of this DOX liposomal formulation, i.e. the set of physicochemical properties resulting from in-cuvette production; this mirrors into the lack of analytical tools that can quantitatively characterize the nanoscale molecular organization of the drug within the intact liposomal formulation upon production (Jiang, et al. In vitro and in vivo characterizations of PEGylated liposomal doxorubicin. Bioanalysis 3, 333-344 (2011)).

General consensus has been reached that the crystalline form of DOX within lipid vesicles (i.e. nanorod-shaped crystals of ammonium-sulfate DOX) is one of the major rate-limiting factors of liposomal DOX efficacy. In fact, crystalized DOX may induce rupture of lipid vesicles with the consequent extracellular release of a fraction of the transported load. Moreover, it was suggested that the crystalized form of the drug exhibit limited ability to enter the nucleus and, most importantly, to interact effectively with DNA, as compared to its monomeric counterpart. Yet, it cannot be excluded that additional molecular states of the same drug (i.e. free drug, drug bound to lipid membrane and crystalline drug) are concomitantly present within the formulation and that such states evolve in time or upon interaction with living cells. As a general consequence, beyond the present example, precise understanding of the drug nanoscale structure/organization/phase within the nanoparticle-based formulation is a major pharmaceutical challenge and would facilitate the development of new drug formulations. To date, referring to the particular case-study discussed (encapsulated Doxorubicin), particle characterization techniques such as Electron Microscopy and solution X-ray scattering only provide semi-quantitative structural information when different drug phases (e.g. free drug and crystalline drug) coexist within a single liposomal formulation. The electron-density profiles of liposomal Doxorubicin obtained by solution X-ray scattering allow to distinguish between empty and drug-loaded nanoliposomes and to probe the structure of the drug inside the liposomes. However, the typical resolution of X-ray scattering is not sufficient to distinguish coexisting phase-separated domains of the drug, even less to quantify the presence of the sub-populations. Such limitations do impact on our ability to monitor the actual nature of a drug delivered with a nanoparticle and hinder the probing of properties that are critical to the compound performance in drug-delivery applications. It therefore remains necessary to implement analytical procedures capable to adequately characterize the in vitro and in vivo supramolecular organizations of the drug within the nanoparticles and their relative properties. New possibilities open up in the case that the drug is a luminescent chemical compound, i.e. a compound that upon irradiation with electromagnetic radiation can re-emit electromagnetic radiation with a detectable lifetime, which is the characteristic time of the radiation emission. Among the properties of luminescence, luminescence lifetime is exquisitely sensitive to a series of physicochemical parameters affecting the nanoscale proximity of the emitting compound and, as such, is potentially informative of the nanoscale molecular organization of the emitting compound (e.g. self-aggregated, bound to other structures/molecules, free in solution, etc.).

Hints on the potential of lifetime analysis are contained, for instance, in In Shah et al. (Sunil Shah et al., Photophysical characterization of anticancer drug Valrubicin in rHDL nanoparticles and its use as an imaging agent J Photochem Photobiol B. 2016 February; 155: 60-65). The authors describe the characterization of the anticancer drug Valrubicin (a fluorescent drug) embedded into nanoparticles. Among the vast toolbox of techniques employed, the authors use also fluorescence lifetime analysis but with the specific aim to distinguish free (unencapsulated) Valrubicin from encapsulated Valrubicin. In particular, lifetime analysis is applied to distinguish a binary macroscopic parameter indicating whether Valrubicin is encapsulated or not. The authors fail to address the supramolecular organization of the drug within the nanoparticles, i.e. provide a 'nanoscale' parameter indicating how luminescent molecules organize in the case of nanoparticles. It is important to stress that molecular organization states of luminescent molecules cannot be binary and are characteristically more than two. In particular, the authors apply lifetime analysis to a substance whose exact organization is not uniform. This causes a subsequent more complex analysis of the lifetime results, i.e. a fourth-order exponential result for a so-called 'non-coupled' Valrubicin. It is important to note that the authors describe an approach wherein a fourth-order exponential lifetime result is interpreted as an 'incorporated' state compared to a third-order exponential lifetime result associated to 'free Valrubicin', defined as Valrubicin dissolved in a buffer suitable for increasing drug solubility. Furthermore, as a matter of fact, the three lifetime parameters of 'free Valrubicin' expressed in nanoseconds are different from the first three lifetime parameters of 'incorporated Valrubicin', which leaves still open the issue of a precise interpretation of how 'incorporated Valrubicin' is organized at a nanoscale level. Indeed, the scope of the authors is to address problems in the context of therapeutic effect of 'free and incorporated' Valrubicin.

SUMMARY

The present invention refers to collecting lifetime decay data characteristic of a pure or nearly pure organization state of molecules and nanocarriers within a standard or reference substance. In some instances, such data are monoexponential decay data. Furthermore, such data may be present in the literature or be collected in an experiment where the reference substance is prepared in order to show a pure or nearly pure organization state. Following the acquisition of one or more reference lifetime data, a comparison to the lifetime decay data of the substance under test is operated. Further to such comparison, in order to have a higher level of precision, additional steps are provided in order to provide information at the nanoscale level about organization states present in the substance under test.

In particular, the invention relates to a first case wherein the organization states of the test substance are unknown, thereby providing a method to find such states (claims 1-3); and to a second case wherein organization states within the test substance are already known, e.g. from literature, but fractional intensity for each of the known states needs to be determined (claim 4).

The methods according to the invention may be automatized to provide fast results in lab testing as well as quality tests of production substances, e.g. drugs, nutraceutical/dietary supplements, cosmetic agents, inks, paint, dyes to be used in several fields as agrochemicals (e.g., controlled-release pesticides), industrial chemicals (e.g., paints, adhesives, inks, anti-counterfeiting inks, cosmetics) and, more recently, textiles.

Panel B) The experiment on spin-coated Doxil-like nanoparticles demonstrates that DOX adsorbed on the liposome membrane has a lifetime signature compatible with expectations, i.e. monoexponential at 4.5 ns.

Figure 4A:
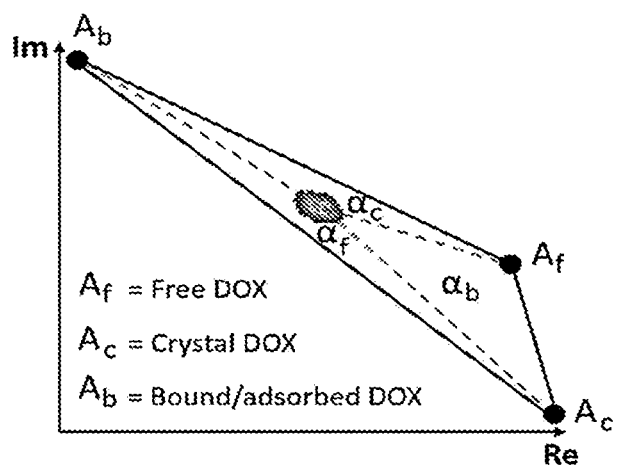
Figure 4B:
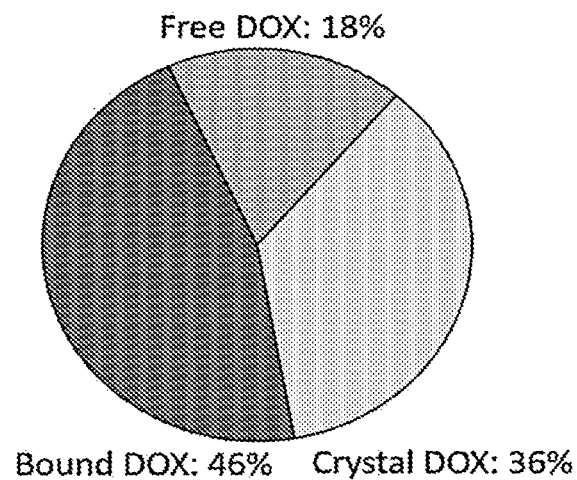

FIGS. 4A and 4B. The fractional intensity contribution of the three identified states of DOX within tested nanoparticles represented both by the schematic triangle representation (left) and by a pie-chart (right); relative intensity of DOX conjugate with the lipids (46%), in blue the relative intensity of free DOX (18%) and in green the relative intensity of DOX organized into nanorod crystals (36%)

DETAILED DESCRIPTION OF THE EMBODIMENTS

The present invention relates to a method for the quantitative determination by lifetime analysis of target luminescent molecules and more specifically of the supramolecular organization of target luminescent molecules encapsulated within, included in or loaded onto nanocarriers.

The method according to the invention is directed to the study of test substances, including nanocarriers loaded with or encapsulating target luminescent molecules having an unknown supramolecular organization. With the expression "supramolecular organization" of the molecule is meant the spatial organization of the plurality of target luminescent molecules encapsulated within, included in or loaded onto the nanocarrier; as non-limitative examples of possible states the molecules can be self-aggregated, bound to other structures/molecules, free in solution, crystallized etc.

Within the scope of this invention the term "nanocarrier", is used alongside "nanoparticle-based structure", "nanosystem", "nanocapsule", "nanosphere", "nano-based formulation", "nanoparticle" and other terms and expressions known to the expert in the field to include any carrier that is meant to be formed and loaded with or can encapsulate or include one or multiple agents and that have one or more dimensions in the nanoscale. The term "encapsulated" will be used, within the scope of the invention, to indicate any form of relation of the molecules with the nanocarrier structure, it will therefore also stand for "included" "loaded" "inserted" "embedded" "adsorbed" "bound" "chemically linked" etc.

As non-limitative examples nanocarriers can be both synthetic and natural polymer-based nanoparticles, nanostructured lipid carriers, lipid-based nanoparticles, solid lipid nanoparticles, liposomes, dendrimers, mesoporous silica nanoparticles micelles, nanoemulsions, polymeric nanoparticles, metallic nanoparticles, surfactant-based emulsions, peptide or protein-based particles, nanoparticles that are formed using a combination of nanomaterials such as mixed lipid-polymer nanoparticles.

If the nanocarrier according to the invention is also formed by luminescent components, said components should not have a excitation/emission spectra overlapping with the target. luminescent molecule's one.

The structures according to the invention can assume different shapes such as spheroidal, cuboidal, pyramidal, oblong, cylindrical, toroidal etc., the shape assumed doesn't limit the application of the method according to the invention.

As stated above such structures can be loaded with or can encapsulate or include one or more than one luminescent agents, such as, but not limited to, therapeutic or diagnostic agents such as doxorubicin, paclitaxel and bleomycin, molecules used in the nutraceutical and dietary supplement fields such as quercetin and flavonoids, cosmetic agents, inks, paint, dyes to be used in several fields as agrochemicals (e.g., controlled-release pesticides), industrial chemicals (e.g., paints, adhesives, inks, anti-counterfeiting inks, cosmetics) and, more recently, textiles.

Within the scope of the invention the expressions "luminescent components" "luminescent molecules" or "luminescence agents" are used to indicate agents, components of the nanostructures and chemical compounds that upon irradiation with electromagnetic radiation can re-emit electromagnetic radiation with a detectable lifetime. In particular electromagnetic radiation having a wavelength included between 300 and 1200 nm, preferably 350 and 1000 nanometres, more preferably between 400 and 700 nm.

The luminescent molecules according to the invention are preferably fluorescent and phosphorescent molecules, more preferably fluorescent molecules.

The method according to the invention is used to determine in a non-perturbative way the supramolecular organization of one or more luminescent agents loaded, incapsulated or included in a nanostructure provided that, if multiple agents are present, the intervals of wavelengths emitted upon irradiation are not too overlapping and therefore indistinguishable.

In a preferred embodiment the nanostructure is loaded with or encapsulate or include a single agent.

By Lifetime Imaging Microscopy is meant a technique to map the spatial distribution of nano-to-millisecond excited state lifetimes within microscopic images. Lifetime Imaging Microscopy systems have been implemented both in the time domain, using pulsed excitation sources and time-correlated or time-gated detection (including, but not limited to, Digital Frequency Domain (DFD)-based detection cards), and in the frequency domain, using sinusoidally intensity-modulated excitation light and modulated detectors. This approach can be applied to both Fluorescence (i.e. Fluorescence Lifetime Imaging Microscopy, or FLIM) and Phosphorescence (i.e. Phosphorescence Lifetime Imaging Microscopy, or PLIM). Particularly preferred is the Fluorescence Lifetime Imaging Microscopy (FLIM). In a preferred embodiment, a raster-scan confocal microscope is used to image the sample, so that lifetime data can be acquired in many points (i.e. pixels) in space. This in turn allows increasing the statistics, and therefore the accuracy, in the measurement (please note, in fact, that accuracy is inversely proportional to the squared root of the number of acquired photons 'N').

The proposed invention allows therefore the characterization of the supramolecular organization of the molecules loaded onto or incorporated into the nanocarrier in a non-perturbative way. As such, it is of primary potential interest for several industries as a methodological platform to quantitatively and rapidly screen the nano-formulation in terms of supramolecular organization of the loaded/encapsulated agent and, based on obtained results, plan rational modification of the production/synthetic process. In particular pharmaceutical industries and companies are interested in including this procedure along quality-control workflow of their drug-manufacturing process.

It is therefore the object of the invention a process aimed at extracting quantitative information on the supramolecular states of a molecule nano-encapsulated in a carrier, the only requisite being that the molecule is a chemical compound that upon irradiation with electromagnetic radiation can re-emit electromagnetic radiation with a detectable lifetime. As stated above, are considered within the scope of the invention electromagnetic radiation having a wavelength ranging between 300 and 1200 nm, preferably 350 and 1000 nanometres, more preferably between 400 and 700 nm, for simplicity we shall use the term luminescence to describe this process and use the term light to indicate said electromagnetic radiation, regardless of its wavelength.

As stated above, among the properties of fluorescence, fluorescence lifetime (i.e. the characteristic time of the radiation emission) is exquisitely sensitive to a series of physicochemical parameters including those affecting the nanoscale proximity of the emitting molecule, such as its supramolecular organization (e.g. self-aggregated, bound to other structures/molecules, free in solution, etc.).

The method according to the invention is based on the use of Lifetime Imaging Microscopy in order to assess in a non-perturbative way the supramolecular organization of a plurality of luminescent molecules encapsulated within, included in or loaded onto the nanocarrier. For example, it is known that a number of substances having each a pure nanoscale organization, e.g. 'free floating' wherein the molecule is encapsulated in the nanocarrier to float free in solution in and out the nanocarrier, provide a mono-exponential lifetime analysis result; instead a substance having mixed or non-pure organization, e.g. a mix of at least two organization states, cannot provide mono-exponential lifetime analysis results.

A further aspect of the invention is that the supramolecular organization for which quantitative information is collected is firstly assumed; then quantified by exponential decay of a lifetime analysis in an initialization step where an initialization substance is prepared so as to include 100% of the assumed supramolecular organization; and later compare the result of the initialization step with the result of a lifetime analysis applied to a test substance wherein the supramolecular organization is unknown yet. The lifetime data of the initialization substance and the test substance (obtained either by fitting the exponential decay or by the phasor-transformation of the decay) can be compared quantitatively using standard statistical tools, e.g. the T-test to evaluate the null hypothesis such that the means of the two populations are equal (if the statistics of the two populations follows a normal distribution).

According to the above, the method of the invention is also applicable iteratively by adding, at each iteration, a new supramolecular-organization state whose exponential decay data are compared to those of the test substance in order to assess a fractional intensity contribution. The number of added supramolecular-organization states and the related number of iterations is determined based on the obtained results at each iteration (see below). Furthermore, the method is also applicable with a single starting supramolecular organization i.e. the first assumed supramolecular organization, in order to check whether the fractional intensity contribution of the test substance supramolecular organization is 100% of the first assumed supramolecular organization. This is helpful e.g. for a rapid quality test during mass production of the test substance.

The method according to a further embodiment of the invention includes the following fundamental steps:

(1) Defining at least a first and preferably a second putative supramolecular standard organization of a plurality of target luminescent molecules and/or the nanocarrier particles wherein the molecules and/or the nanocarrier particles are purely or nearly purely organized and the molecules and/or optionally the nanocarrier particle is also luminescent.

By standard supramolecular organization is meant a pure supramolecular organization of the molecules also including its possible association with the relative nanocarrier and its components, such as but not limited to 100% crystal, 100% solution, 100% associated with the nanocarrier surface/structure.

(2) Receiving a first and preferably a second reference luminescence lifetime dataset representing the at least first and second supramolecular organization of the target luminescent molecules and/or the nanocarrier particles.

(3) Dissolving the nanocarrier containing the luminescent molecule under study in its natural solvent and placing it under the proper light excitation source.

The choice of the proper light excitation source and of the proper excitation wavelength is within reach of the expert in the field—

(4) Measuring luminescence lifetime.

Luminescence lifetime is measured using any suitable method and instrument known to the expert in the field. Luminescence lifetime is measured either in the time domain, using pulsed excitation sources and time-correlated or time-gated detection, or in the frequency domain, using sinusoidally intensity-modulated excitation light and modulated detectors.

(5) Analysing the luminescence lifetime. The analysis can be performed either by fitting the lifetime decay or by the phasor approach to lifetime data. In the case that decay-fitting is chosen as analytical tool, data interpolation by mono or multi-exponential functions will be used, according to the general Equation below:

$$A(t) = \sum_{i=1}^{n} A_i e^{-t/\tau_i} \quad \text{Eq. 1}$$

Where $A_i$ indicates the series of pre-exponential factors (i.e. the fractional intensity contribution of each supramolecular configuration state considered), t is time, $\tau_i$ is the characteristic lifetime of each supramolecular configuration state considered. It is important to note that fitting operation according to the present invention requires the calculation of $A_i$ (pre-exponential factors or weights) whereas, during each fitting operation, $\tau_i$ is already assigned based on the i-th standard substance including the i-th putative organization state.

The exact number of exponentials to be used for proper fitting will be selected based on the goodness of the data interpolation obtained case by case. Fit goodness, in turn, will be assessed by the operator by using standard fit output parameters, such as 'chi square' ($\chi_R^2$), fit residuals and, eventually, fit-residuals autocorrelation analysis (to check whether residuals are randomly distributed).

In a preferred embodiment, the phasor approach to lifetime data is used as a fit-free, fast, graphical method to extract the quantitative information encrypted in the lifetime measurements (Digman, et al. "The phasor approach to fluorescence lifetime imaging analysis." Biophys. 2008). As an example, in phasor analysis of data acquired in the time domain, the fluorescence lifetime spectra of each pixel in the image is mapped onto a "phasor" plot that is made up out of two numbers: the real and imaginary parts (amplitude and phase respectively) of the first harmonic of the Fourier transform of the fluorescence lifetime, with no need for lifetime-decay data fitting. This is a complex function and drawing the imaginary versus real part of this function for all possible lifetimes will be a semicircle where the zero lifetime is located at (1,0) and the infinite lifetime located at (0,0). By changing the lifetime from zero to infinity the phasor point moves along a semicircle from (1,0) to (0,0). This suggests that by taking the Fourier transformation of a measured decay curve, the lifetime can be estimated based on the position of the phasor on the semicircle. This facilitates the analysis since each decay is transformed into a unique position on the phasor plot which depends on the average lifetime. The semicircle identifies all possible monoexponential decays. When the measured decay, instead, consists of a superimposition of different monoexponential components, the resulting phasor falls inside the semicircle, in a position that depends on the fractional contributions of the components (see below). In view of the above, lifetime data of a standard organization state having a monoexpometial decay fall on the universal circle. Each lifetime measurement, being typically performed in multiple points (i.e. pixels) in space, will yield a distribution of data-points in the phasor plot whose dispersion will reflect the intrinsic uncertainty in the measurement (that is inversely proportional to the squared root of the number of acquired photons 'N') and the intrinsic heterogeneity, if any, of the measured lifetime. Data-points in the phasor plot, then, can be analysed by standard statistical tools (e.g. Principal Moment analysis of multivariate data) to extract the relevant parameters of the distribution.

(6) Quantitatively comparing the test luminescence lifetime dataset and the at least first and second reference luminescence lifetime dataset to obtain the relative fractional intensity contributions of the first and the second supramolecular organization within the test substance. In the case of decay fitting by exponentials, the fractional contributions of the first and the second supramolecular organization are extracted by fixing the characteristic lifetimes of the two species in the fitting procedure and retrieving the pre-exponential coefficients (i.e. A coefficients in Eq. 1).

Where only the first reference luminescence lifetime dataset is present, it is possible to assess a 100% fractional intensity of the first organization state if the reference data and the test data are superimposed. Otherwise, a further organization e.g. second organization state shall be assumed, lifetime data thereof shall be collected and step 6 of comparing is completed according to the previous paragraph. Additional iterations are possible depending on the result of the comparison.

In a preferred embodiment, the fractional intensity contribution of all the supramolecular organizations considered is extracted in a fit-free, graphical manner, by applying simple algebraic rules to the phasor-plot dataset (a dedicated routine is available in the SimFCS software, free download at www.lfd.uci.edu).

Referring to step 2, a preferred approach to find the reference is to perform dedicated lifetime analysis in order to find the lifetime analysis parameter value(s) of each standard supramolecular organization to be considered in the subsequent test lifetime analysis, where an unknown supramolecular organization is tested. In doing so, Steps (1) to (3) are repeated in the same order for all those supramolecular organizations of the luminescent molecule (obtained in the form of pure, separate standards) which are thought to be present within the nanocarrier under study (e.g. free molecule, crystalized molecule, etc.). These reference standards will delineate a portion of the phasor plot within which the nanocarrier under study will lie. Simple algebraic rules will be applied to extract the fractional-intensity contribution of each of the standards. In a preferred embodiment, the number of standards is included between 1 and 4, although there is no physical limit to the number of components. As an example, the phasor of a decay consisting of a linear combination of three pure components falls inside the triangle and the fractional intensities of the components can be retrieved (see Refs. 6, 7 for more details).

The procedure described presents selected advantages with respect to alternative strategies. In detail:

- It is a label-free procedure, i.e. it does not require chemical modification of the drug formulation to introduce fluorescent probes but exploits intrinsic signals. It affords a quantitative description of the drug formulation in its native state
- It does not require chemical fixation of the sample as in the case, for instance, of Electron Microscopy. When visible light can be used it allows the investigation of the drug formulation dissolved directly in its optimal dilution solution.
- It affords nanoscale sensitivity (to molecular organization) in a standard, diffraction-limited, optical microscopy setup, with no need to use super-resolution strategies. This depends on the exquisite sensitivity of the lifetime parameter to the fluorophore nanoscale environment and/or organization.
- It can rely on fast, robust, fit-free, and fully-graphical data-analysis procedures (if phasor approach is used).
- It is highly flexible in terms of range of applications, from in-cuvette assays to in vivo experiments.
- It can be applied to any molecule/drug/compound capable to absorb photons at a certain wavelength, and emit photons with a detectable lifetime
- If combined with a complete spectroscopic characterization of the emitting species (e.g. by absorption/fluorescence spectroscopy to derive the absorption spectrum and quantum yield of all emitting species in their isolated form) the procedure described here leads to the calculation of the fractional populations (i.e. stoichiometry) of emitting species within the formulation.
- It may allow to detect changes in the liposomal drug structure induced by interaction with bodily fluids (e.g. human serum). This is relevant in order to mimic in vivo conditions thus contributing to understand the drug behavior in the human body.
- Depending on the specific wavelengths used, it may allow the detection of changes in the liposomal drug structure in compartments of living cells (cytosol, nucleus etc.) where particle characterization techniques cannot be applied.

The following example is to be regarded as being illustrative of the invention and does not limit its corresponding scope

EXAMPLES

Determination of the Supramolecular Organization of DOX Encapsulated in a Liposomal Nanocarrier:

In order to better clarify the object of the invention, the method will be described in in a specific application to a PEGylated liposomal formulation of Doxorubicin, namely Doxoves®. Like many other chemotherapeutic agents, Doxorubicin shows a peculiar fluorescence emission upon excitation by visible light. Based on manufacturer's indications most of the DOX molecules (~98%) are encapsulated within the aqueous liposome lumen in the form of nanorod-shaped crystals of ammonium-sulfate-DOX salt, with the remaining minor fraction (~2%) of molecules free in solution. Please note that this latter minor fraction is selectively quenched by potassium iodide (KI), opportunely dissolved in solution. This in turn allows the specific analysis of the DOX molecules encapsulated within the nanocarrier.

Figure 1:
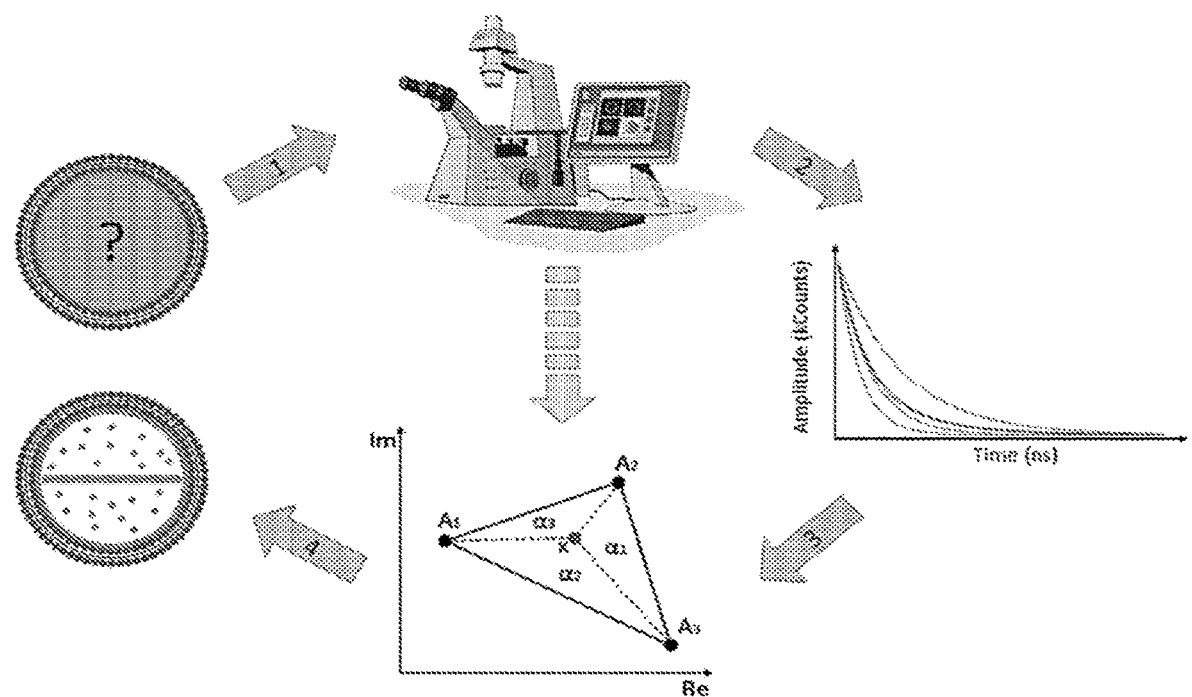
FIG. 1 schematically illustrates the methodology of the invention.
Figure 2:
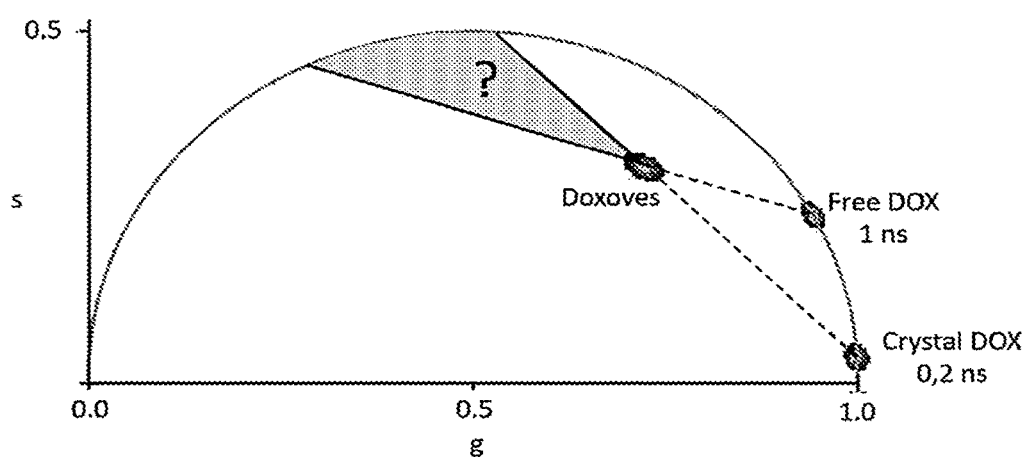
FIG. 2: Phasor clusters for liposomal DOX in the form of Doxoves® (inside the universal circle), purified rod-shaped crystals (0.2 ns) and free DOX in water (1 ns). The continuous black lines select the area of the phasor plot in which a hypothetical third species can lay.
Figure 3A:
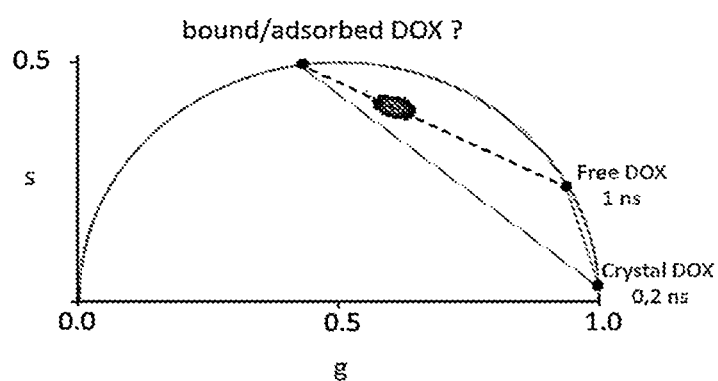
FIGS. 3A and 3B: Panel A) A line starting from Free-DOX and passing through the cluster Doxil-like nanoparticles allows to identify a region of the phasor plot (dashed red line) where a third species shall be located.
Figure 3B:
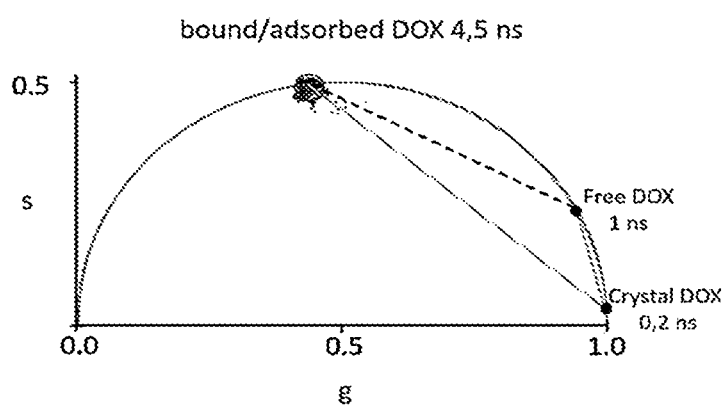

The procedure was applied to Doxoves® as follows:

1) Based on previous knowledge, at least three different supramolecular organizations of DOX molecules are supposed to contribute to the overall nature of Doxoves® nanocarriers: crystallized DOX, free DOX, and DOX eventually associated with the nanocarrier surface, i.e. with lipids. These three forms are defined here as standards.
2) The three standards identified at step 1 are obtained and measured. As a preliminary step, each standard is produced and dissolved in a buffer that is the same as that of the test substance. In the present case, manufacturer's indications were followed to produce the correct buffer composition. In general, substances having an impact on lifetime analysis of the test substance, e.g. Doxoves®, shall be also present in the standard substances. First, the phasor signature of crystalized DOX and free-in-solution DOX are measured: two mono-exponential lifetimes are obtained: 0.2 ns for the crystal and 1 ns for free DOX, respectively. To obtain the third standard, first the protocol by Wei et al. (Wei, X.; Shamrakov, D.; Nudelman, S.; Peretz-Damari, S.; Nativ-Roth, E.; Regev, O.; Barenholz, Y. Cardinal Role of Intraliposome Doxorubicin-Sulfate Nanorod Crystal in Doxil Properties and Performance. ACS Omega 2018, 3 (3), 2508-2517.) was adopted to synthetize a Doxoves® variant (hereafter referred to as similDoxoves®) that does not contain DOX crystals. Then, by spin-coating simil-Doxoves® nanoparticles on a glass surface. This procedure destroys mechanically the liposomal particles and recovers the liposomal membranes on the glass. Consistently with our discussion the phasor-FLIM signature of the recovered membrane patches (i.e. the pure standard of DOX adsorbed on membranes) shows a monoexponential lifetime coincident with that expected (i.e. experimental cluster in FIG. 3B, at 4.5 ns).
3) Doxoves® nanoparticles are dissolved in manufacturer's solution and imaged by exciting at 470 nm and collecting the emission in the 500-650 nm range.
4) Doxoves® characteristic lifetime is measured in the time domain, with a pulsed diode laser operating at 40 MHz and by a photomultiplier tube interfaced with a time-correlated single-photon counting card and setup (PicoHarp 300, PicoQuant, Berlin). It is important to note that lifetime measuring conditions, e.g. temperature, pH etc., shall be the same for measures on the test substance and measures on the standard substances.
5) Doxoves® lifetime data are analysed by the phasor approach. In more detail, the phasor is calculated by using a dedicated routine in the SimFCS software (Laboratory for Fluorescence Dynamics, University of California, Irvine). Doxoves® phasor falls within the universal circle, revealing the multi-exponential nature of the measured fluorescence decay (FIG. 2).
6) Following the general protocol, the three postulated standards are sufficient to explain the experimental results obtained for Doxoves®: in fact, Doxoves® phasor falls within the triangle with vertices the characteristic phasors of the standards. Simple algebraic rules are adopted to extract quantitatively the relative contribution (fractional intensity) of each standard (by a dedicated routine in SimFCS software).

It may still be under question whether there may be more than three organization states, e.g. four defining a trapezoidal shape within the universal circle and circumscribing the location of the test substance lifetime decay within the universal circle. A final control experiment was thus performed to corroborate the hypothesis that only three standard components (and NOT more than three) contribute to the overall organization of encapsulated DOX. In brief, the lifetime of simil-Doxoves® in solution is measured. If only three components contribute to Doxoves® organization, simil-Doxoves® is expected to be a linear combination of just free DOX and DOX associated to nanocarrier lipids, thus lying along the segment that connects these two states. Data confirm the expectations and confirm that DOX molecules associated to nanocarrier lipids have a characteristic mono-exponential fluorescence lifetime of about 4.5 ns (indicated by the point on the universal circle in FIG. 3A).

The application of the method according to the invention to the case study of Doxoves® shows the ability to quantify the relative contribution (measured as fractional intensity contribution) of the different drug supramolecular states to the overall nanoparticle organization and shows the inconsistency of the analyses performed with the existing characterization methods. In fact, so far, the presence of both free DOX and membrane-associated DOX molecules, although postulated, could not be directly measured by available methods (e.g. Electron Microscopy).

Quercetin

Many other molecules/agents with fluorescence properties similar to DOX are commonly encapsulated in polymer micelles to improve their water solubility and/or contribute to develop novel drugs with tailored performances. For instance, Quercetin is a hydrophobic agent with potential anticancer activity. It was encapsulated into several different nanocarriers, among others: chitosan-coated nano-liposomes (Hao et al. LWT—Food Science and Technology Volume 85, Part A, November 2017, Pages 37-44), poly (lactic-co-glycolic) acid (PLGA) nanoparticles (Lozano et al 2019. Nanoencapsulated Quercetin Improves Cardioprotection during Hypoxia-Reoxygenation Injury through Preservation of Mitochondrial Function), biodegradable monomethoxy poly(ethylene glycol)-poly($\varepsilon$-caprolactone) (MPEG-PCL) micelles (Gao et al. Nanoscale. 2012 Nov. 21; 4(22):7021-30). These latter were used to provide a proof-of-principle test in treating ovarian cancer. These Quercetin loaded MPEG-PCL micelles with drug loading of 6.9% had a mean particle size of 36 nm, rendering the complete dispersion of Quercetin in water. Still, no information was retrieved on Quercetin supramolecular organization within these example nanoparticles.

The procedure described in the application allows dissecting quantitatively the supramolecular organization of luminescent molecules in general, loaded or included in or encapsulated into carriers, such as nanoparticles or liposomes. This knowledge, in turn, can be used as quantitative platform to compare different synthetic identities and guide the interpretation of their performances in vitro or in vivo.

The proposed procedure allows the characterization of the nanoscale molecular organization of a drug in a pharmaceutical formulation. As such, it is of potential interest for pharmaceutical industries as a methodological platform to quantitatively and rapidly screen the formulation in terms of drug nanoscale organization and, based on obtained results, plan rational modification of the production/synthetic process. Pharmaceutical industries/companies may be interested in including this procedure in their quality-control workflow of their drug-manufacturing process In view of the above, according to an aspect of the invention, a test to determine the number of organization states of fluorescent target molecules within a test substance is as follows:

Provide first standard lifetime data of a known first putative organization state of given luminescent molecules in the presence of given nanoparticles, said first lifetime data being measured in a first standard substance where the first putative organization state describes nearly 100% or 100% of the aggregation states within the first standard substance, i.e. the fractional intensity of the first putative organization is 100% or nearly 100%. According to the phasor plot approach, this is for example a first point on the circumference of the universal circle. According to the exponential approach, this happens where lifetime is mono-exponential having a first value. More generally, it is important to note that, even in case of a bi-exponential decay, the first standard data refer to a known and theoretically pure organization of the luminescent molecules and the nanoparticles, e.g. data are provided from a substance prepared on purpose and containing theoretically 100% of the first putative organization state; according to a preferred embodiment, the standard substance(s) is prepared based on the composition of the test substance. For instance, where the test substance includes a buffer other than the molecules and the nanocarriers, the composition of such a buffer, e.g. found in the manufacturer's instructions of the test substance, shall be provided in the standard substance(s) so that, at a nanoscale, such buffer is combined with the molecules and the nanocarriers;

Provide test lifetime data of a test substance where the organization states of the target luminescent molecules are unknown;

Compare the standard lifetime data and first test lifetime data: if data are substantially superimposed, then the test substance has a 100% fractional intensity of the putative organization state; if data are not superimposed then:

Provide a second standard lifetime data of a known second putative organization state of the target luminescent molecules in the presence of the nanoparticles, said second lifetime data being measured in a second standard substance where the second putative organization state describes nearly 100% or 100% of the aggregation states within the first standard substance, i.e. the fractional intensity of the second putative organization is 100% or nearly 100%. According to the phasor plot approach, this is e.g. a second point on the circumference of the universal circle spaced from said first point. According to the exponential approach, this happens when lifetime is mono-exponential having a second value different from the first value;

Compare the first and second standard lifetime data and the test lifetime data: if test lifetime data are a linear combination of the first and second lifetime data, then the test substance has only two possible supramolecular organization states and the respective fractional intensity contribution is calculated based on the distance of the test lifetime data point from the two standard lifetime data on the phasor plot: in particular, the fractional contribution of each supramolecular organization state will be inversely proportional to its distance from the test lifetime data, according to the equation:

$$f_i = 1 - \frac{d_{ix}}{d_{12}} \times 100 \qquad \text{Eq. 2}$$

Where $f_i$ is the fractional intensity contribution of one of the two standard species considered (i=1 or 2), $d_{ix}$ is the distance measured on the phasor plot between the test lifetime data and one of the two standard species considered, $d_{12}$ is the total distance between the two standard species considered. Please consider that routine algorithms for such calculations are available in SimFCS software (free download at www.lfd.uci.edu).

As described here, in the phasor approach the linear combination of two species is assessed and resolved graphically. According to the exponential approach, instead, the same linear combination is checked by fitting the test data with Eq. 1 in the form of a multi-exponential function. As an example, if the two standards considered show monoexponential lifetimes, test lifetime data will be fitted by a double-exponential function fixing the characteristic lifetimes of the two standards to the values measured in separate experiments (described above). At this point, the pre-exponential factors $A_1$ and $A_2$ derived from fitting will represent the fractional intensity contribution of the two species, analogously to the what derived from the phasor approach (under the constrain that $A_1+A_2=1$); the same reasoning applies to the case in which the standards are characterized by multiexponentials lifetimes but this will inevitably increase the number of fit variables to consider. if test lifetime data are not a linear combination of first and second standard lifetime data, then:

Provide a third standard lifetime data of a known third putative organization state of the target luminescent molecules in the presence of the nanoparticles, said second lifetime data being measured in a third standard substance where the fractional intensity of the third putative organization is 100% or nearly 100%;

Compare the first, second and third standard lifetime data and the test lifetime data: according to the phasor approach, that for complex analyses like this is preferable because it relies on graphical data e.g. areas, if the test lifetime data lies within a triangular shape connecting on the universal circle the first, second and third lifetime data points, the test substance may show a three-only organization states and a proposed fractional intensity is calculated by calculating the share of each sub-triangle having a vertex in the test substance data and large triangle connecting the three standard lifetime data;

Otherwise, iteratively provide additional standard lifetime data of additional putative organization states within a standard substance having a nearly 100% fractional intensity for the additional putative organization state until test lifetime data, according to the phasor approach, falls within the area of the polygon connecting the plurality of standard lifetime data.

According to a preferred embodiment of the present invention, when the test substance lifetime data fall within the area delimited by the plurality of standard lifetime data, a further step, e.g. a check step, is provided to determine whether potential additional organization states may be present in the test substance. According to such a step, comparison lifetime data are collected from a lifetime analysis of a comparison substance derived from the test substance so as to include, in the case of only three organization states, a mix of the first and second state. Preferably, such a comparison substance is produced on purpose in a laboratory and, according to an embodiment, the example already discussed for simil-Doxoves® can be applied or suitably adapted. In case of only three organization states, once one of them is eliminated, the comparison substance shall only provide a linear combination of the remaining organization states. In the negative, a further (fourth) organization state must be assumed and the corresponding standard lifetime data collected.

The linear combination test that, in case of three only organization states, provides a positive result when comparison substance lifetime data lies on the line of the phasor plot connecting the assumed non-cancelled organization states, can be generalized so that one or more comparison substances are prepared to exclude one or more putative organization states; and a positive result of the check step corresponds to:

the evidence that the comparison substance lifetime data falls within the area delimited by lines connecting the standard data of the organization states that are present in the comparison substance; and the comparison substance lifetime data are provided by a linear combination of the standard data representing pure organization states within the comparison substance. When using the phasor plot, such a linear combination is provided, as mentioned above, by simple fraction operations on distances or areas.

It is also important to note that lifetime analysis is more sensitive where luminescence is high: this means that on absolute values some organization states may receive a higher fractional intensity because of high brightness than that of other 'darker' organization states. However, fractional intensities obtained according to the present invention from different test substances and/or experimental conditions can be compared and the precision of the comparison is very satisfactory. Therefore the invention is more suited to comparing data from different experiments with respect to providing absolute values from each of them.

As shown in the present examples and thanks to the broad application of lifetime analysis for luminescent molecules, the present invention is applicable in fields other than drugs, such as the nutraceutical and dietary fields, cosmetic agents, inks, paint, dyes to be used in several fields as agrochemicals (e.g., controlled-release pesticides), industrial chemicals (e.g., paints, adhesives, inks, anti-counterfeiting inks, cosmetics) and, more recently, textiles.

Furthermore, it is possible that the nanocarrier particle be luminescent instead of the molecule.

Furthermore, it is possible that the nanocarrier particle be luminescent in at least one of its components, instead of the encapsulated molecule.

The method according to the invention, in this case, can be used to determine if the lifetime of the luminescent component of the nanocarrier is affected (and to what extent) by the possible closeness/proximity/interaction with the molecules loaded, incapsulated or included in the nanocarrier. The method can be still sensitive to some of the organization states of the encapsulated molecules with respect to the luminescent component of the nanocarrier, i.e. specifically to those affecting the lifetime of the luminescent component of the nanocarrier. For the sake of clearness, these states will be referred to in the following as "reciprocal organization states" (of the encapsulated molecule with respect to the luminescent component of the nanocarrier.

The method according to a further embodiment of the invention includes the following fundamental steps:

(1) Defining at least a first and preferably a second putative reciprocal organization state of the encapsulated molecule with respect to the luminescent component of the nanocarrier.

By reciprocal organization state is meant a pure supramolecular organization of the molecules also including its possible association with the relative nanocarrier and its components, such as but not limited to 100% crystal, 100% solution, 100% associated with the nanocarrier surface/structure.

(2) Receiving a first and preferably a second reference luminescence lifetime dataset representing the at least first and second reciprocal organization.

(3) Dissolving the nanocarrier containing its luminescent component (and the encapsulated molecules) in its natural solvent and placing it under the proper light excitation source.

The choice of the proper light excitation source and of the proper excitation wavelength is within reach of the expert in the field—

(4) Measuring luminescence lifetime.

Luminescence lifetime is measured using any suitable method and instrument known to the expert in the field. Luminescence lifetime is measured either in the time domain, using pulsed excitation sources and time-correlated or time-gated detection, or in the frequency domain, using sinusoidally intensity-modulated excitation light and modulated detectors.

(5) Analysing the luminescence lifetime. The analysis can be performed either by fitting the lifetime decay or by the phasor approach to lifetime data. In the case that decay-fitting is chosen as analytical tool, data interpolation by mono or multi-exponential functions will be used, according to the general Equation 1 above.

The exact number of exponentials to be used for proper fitting will be again selected based on the goodness of the data interpolation obtained case by case (see above in the text for more details). In a preferred embodiment, as explained above, the phasor approach to lifetime data is used as a fit-free, fast, graphical method to extract the quantitative information encrypted in the lifetime measurements (Digman, et al. "The phasor approach to fluorescence lifetime imaging analysis." Biophys. 2008).

(6) Comparing the test luminescence lifetime dataset and the at least first and second reference luminescence lifetime dataset to obtain the relative fractional intensity contributions of the first and the second supramolecular organization within the test substance. In the case of decay fitting by exponentials, the fractional contributions of the first and the second supramolecular organization are extracted by fixing the characteristic lifetimes of the two species in the fitting procedure and retrieving the pre-exponential coefficients (i.e. A coefficients in Eq. 1).

Where only the first reference luminescence lifetime dataset is present, it is possible to assess a 100% fractional intensity of the first organization state if the reference data and the test data are superimposed. Otherwise, a further organization e.g. second organization state shall be assumed, lifetime data thereof shall be collected and step 6 of comparing is completed according to the previous paragraph. Additional iterations are possible depending on the result of the comparison. In particular, steps (1) to (3) are repeated iteratively in the same order for all those reciprocal supramolecular organizations of the luminescent component of the nanocarrier with respect to the encapsulated molecules (obtained possibly in the form of pure, separate standards) which are thought to be present within the nanocarrier under study. Furthermore, possible additional steps applicable for luminescent nanoparticles are the ones, suitably adjusted, already described above for luminescent molecules. In particular, as for the case of luminescent molecules, also for luminescent nanocarriers it is possible to analyze lifetime data either as fitting data of exponential decay or graphical phasor-based data.

What is claimed is:

1. A determination method of a supramolecular organization of target luminescent molecules encapsulated within nanocarrier particles by a lifetime analysis comprising the steps of:

defining at least a first supramolecular organization of a plurality of target luminescent molecules and/or the nanocarrier particles, wherein the plurality of target luminescent molecules and/or the nanocarrier particles are substantially organized and optionally the nanocarrier particle is further luminescent;

receiving at least a first standard luminescence lifetime dataset representing a first decay associated to a first standard substance where the plurality of target luminescent molecules and/or the nanocarrier particles are substantially organized according to the first supramolecular organization;

processing a test substance comprising nanocarriers with the plurality of target luminescent molecules to obtain a test luminescence lifetime dataset of the test substance comprising a target luminescent molecule having an unknown supramolecular organization;

quantitatively comparing the test luminescence lifetime dataset and the at least first standard luminescence lifetime dataset;

determining whether a second supramolecular organization of the plurality of target luminescent molecules and the nanocarrier particles is present or not in the test substance based on a quantitative superimposition of the test luminescence lifetime dataset and the first standard luminescence lifetime dataset.

2. The determination method according to claim 1, wherein:

the step of defining comprises at least a second or more supramolecular organizations of the plurality of target luminescent molecules;

the step of receiving comprises a second or more standard luminescence lifetime datasets representing a second decay associated to a first standard substance where the plurality of target luminescent molecules and/or the nanocarrier particles are substantially organized according to the second or more supramolecular organizations; and the step of determining comprises whether a further supramolecular organization of the plurality of target luminescent molecules and/or the nanocarrier particles is present in the test substance based on whether test substance luminescence lifetime data is a linear combination of the standard luminescence lifetime dataset.

3. The determination method according to claim 2, further comprising the steps of:

identifying a number of iterations for at least two supramolecular organization states;

collecting comparison luminescence lifetime data from a comparison substance generated so as not to show at least one of the at least two supramolecular organization states of the plurality of target luminescent molecules and the nanocarrier particles; and comparing the test substance luminescence lifetime data and the comparison luminescence lifetime data to confirm whether the number of iterations indicates a total number of standard supramolecular organization states of the plurality of target luminescent molecules present within the test substance.

4. The determination method according to claim 3, wherein the luminescence lifetime data are either fitted exponential decay data or phasor plot data.

5. The determination method according to claim 4, wherein a fitting exponential decay comprises the calculation of a i-th weight $A_i$ attributable to each i-th putative organization state and a i-th characteristic lifetime attributable to each i-th putative organization state is already assigned from an i-th standard luminescence lifetime dataset obtained in the step of receiving.

6. The determination method according to claim 1 comprising an additional step of quantifying a fractional intensity contribution of each defined supramolecular organization of the plurality of target luminescent molecules and/or the nanocarrier.

7. The determination method according to claim 1, wherein the target luminescent molecule or nanocarrier is a drug.

8. The determination method according to claim 1, wherein standard luminescence lifetime data are monoexponential.

* * * * *